United States Patent
Mizutani et al.

(10) Patent No.: US 6,673,985 B2
(45) Date of Patent: Jan. 6, 2004

(54) SANITARY NAPKIN

(75) Inventors: Satoshi Mizutani, Kagawa (JP); Etsuko Tagami, Kagawa (JP); Kazuya Nishitani, Kagawa (JP); Makoto Suekane, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 231 days.

(21) Appl. No.: 10/021,804

(22) Filed: Nov. 8, 2001

(65) Prior Publication Data

US 2002/0062116 A1 May 23, 2002

(30) Foreign Application Priority Data

Nov. 21, 2000 (JP) ........................................ 2000-354201

(51) Int. Cl.$^7$ ................................................. A61F 13/15
(52) U.S. Cl. ........................ 604/380; 604/379; 604/378; 604/385.01; 604/305.04
(58) Field of Search ............................ 604/385.01, 379, 604/380, 385.101, 385.28, 378, 385.04

(56) References Cited

U.S. PATENT DOCUMENTS

| | | |
|---|---|---|
| 5,704,928 A | 1/1998 | Morita et al. |
| 5,810,800 A | 9/1998 | Hunter et al. |
| 6,159,190 A * | 12/2000 | Tanaka et al. ......... 604/385.24 |
| 2002/0165512 A1 * | 11/2002 | Drevik et al. ............... 604/380 |

FOREIGN PATENT DOCUMENTS

| | | |
|---|---|---|
| EP | 0 953 326 A2 | 11/1999 |
| EP | 0 985 396 A2 | 3/2000 |
| JP | 10-372066 | 12/1998 |

* cited by examiner

*Primary Examiner*—Weilun Lo
*Assistant Examiner*—Jacqueline F Stephens
(74) *Attorney, Agent, or Firm*—Darby & Darby

(57) ABSTRACT

Disclosed is a sanitary napkin having a longitudinal rear portion. The sanitary napkin includes: a main absorbent region having a main absorbent core between a back sheet and a surface sheet; side regions on both sides of the main absorbent region; and boundary regions having leakage-preventing side walls and positioned between the main absorbent region and the side regions. In the rear portion, the main absorbent region has a stiff portion, and the side regions are protruded laterally to form rear flaps each having an auxiliary absorbent core between the back sheet and another sheet. In the rear portion, a portion of the main absorbent region having the stiff portion therein, the boundary region and the rear flap have different longitudinal stiffnesses according to the following relationship: the portion having the stiff portion therein>the boundary region>the rear flap.

8 Claims, 5 Drawing Sheets

SANITARY NAPKIN

BACKGROUND OF THE INVENTION

1. Field of the Invention

The present invention relates to a sanitary napkin and, more particularly, to a sanitary napkin having a rear portion, which is enhanced in prevention of liquid leakage therefrom and in fitness on the body of a wearer.

2. Description of Related Art

For example, a sanitary napkin, as disclosed in Japanese Unexamined Patent Publication No. 2000-189459, is provided at its longitudinal rear portion with flap portions shaped to bulge laterally from both sides of an absorbent main body. The absorbent main body is provided at its lateral center with an absorbent core, and the flap portions are provided with absorbent cores separate from that in the absorbent main body.

In this sanitary napkin, the menstrual blood having oozed to the rear portion of the absorbent main body corresponding to the buttocks of the wearer's body can be absorbed by the flap portions. As a result, the sanitary napkin can prevent the sideway leakage of the liquid at its rear portion.

At the rear portion of the sanitary napkin disclosed in the Unexamined Publication, however, the boundary portions between the absorbent core in the absorbent main body and the absorbent cores in the flap portions are given an easily deformable structure. If a twisting force or the like is applied to the rear portion of the sanitary napkin during wear, particularly by the turn-over of a wearer in sleep, therefore, the absorbent core in the absorbent main body is easily deformed at first, and there is a danger of deformation that the flap portions may be slid or folded back toward the center to overlap the central portion.

As the flap portions overlap the liquid receiving side of the central portion, the rear portion is obstructed from absorbing the menstrual blood and allows the sideway leakage. Moreover, the fitness of the sanitary napkin is lost to give an uncomfortable feeling to the buttocks of a wearer.

SUMMARY OF THE INVENTION

The present invention has been worked out in view of the shortcoming in the prior art set forth above. It is therefore an object of the present invention to provide a sanitary napkin which is enabled to prevent the sideway leakage from its rear portion effectively without losing the fitness by preventing rear flaps from being deformed toward its central portion while it is worn, particularly in sleep.

According to the invention, there is provided a sanitary napkin having a longitudinal rear portion to be applied to the buttocks of a wearer, comprising:

a longitudinally extending main absorbent region in which a longitudinally extending main absorbent core is disposed between a liquid-impermeable back sheet and a liquid-permeable surface sheet;

side regions positioned on both sides of the main absorbent region; and boundary regions between the main absorbent region and the side regions, each boundary region being provided with a longitudinally extending leakage-preventing side wall, wherein in the rear portion, at least a portion of the main absorbent region is formed into a stiff portion having a stiffness higher than that of the remaining portion of the main absorbent region, and in the rear portion, the side regions are protruded laterally to form rear flaps, in each of which an auxiliary absorbent core is disposed between the back sheet and a sheet positioned on a surface side opposite to the back sheet with respect to the auxiliary absorbent core, wherein in the rear portion, a portion of the main absorbent region having the stiff portion therein, the boundary region and the rear flap have different longitudinal stiffnesses according to the following relationship: the portion of the main absorbent region having the stiff portion therein>the boundary region>the rear flap.

For example: the portion of the main absorbent region having the stiff portion therein has a stiffness of 9.8 to 29.4 mN; the boundary region has a stiffness of 3.94 to 8.8 mN; and the rear flap has a stiffness of 0.49 to 3.43 mN.

In the rear portion, preferably, the main absorbent core is compressed at least partially to form the stiff portion. More preferably, the main absorbent core is partially compressed in the rear portion so that the stiff portion extends linearly in the longitudinal direction. Alternatively, the main absorbent core, as prepared to be relatively thick in advance, may be substantially entirely compressed at a portion positioned in the rear portion so that the main absorbent core may have a higher stiffness in the rear portion than in a portion forwardly thereof, thereby to provide a stiff portion which coincides with the substantially entire area of a portion of the main absorbent region positioned in the rear portion.

Preferably, each leakage-preventing side wall is folded and secured in the rear portion so as not to allow of rising thereof, but is allowed to rise from the surface side in a portion forwardly of the rear portion.

Preferably, folding portions for facilitating folding of the rear flaps are formed on boundary lines between the boundary regions and the rear flaps. The main absorbent core and the auxiliary absorbent cores may be separated from one another at the folding portions.

Each auxiliary absorbent core may be split into a plurality of segments.

The sanitary napkin of the invention is provided, at its rear portion having the rear flaps, with the stiff portion in the main absorbent region. Therefore, the main absorbent region is hardly deformed when a twisting force acts on the sanitary napkin. On the other hand, the boundary regions between the main absorbent region and the rear flaps are given a bulky structure with the leakage-preventing side walls and a higher stiffness than the rear flaps. When the twisting force acts, therefore, there hardly occurs the deformation in which the rear flaps are folded or slid to overlap the main absorbent region. On the other hand, the rear flaps are easily deformed to fit on the buttocks of a wearer.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENTS

The present invention will be discussed hereinafter in detail in terms of the preferred embodiment of a sanitary napkin according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
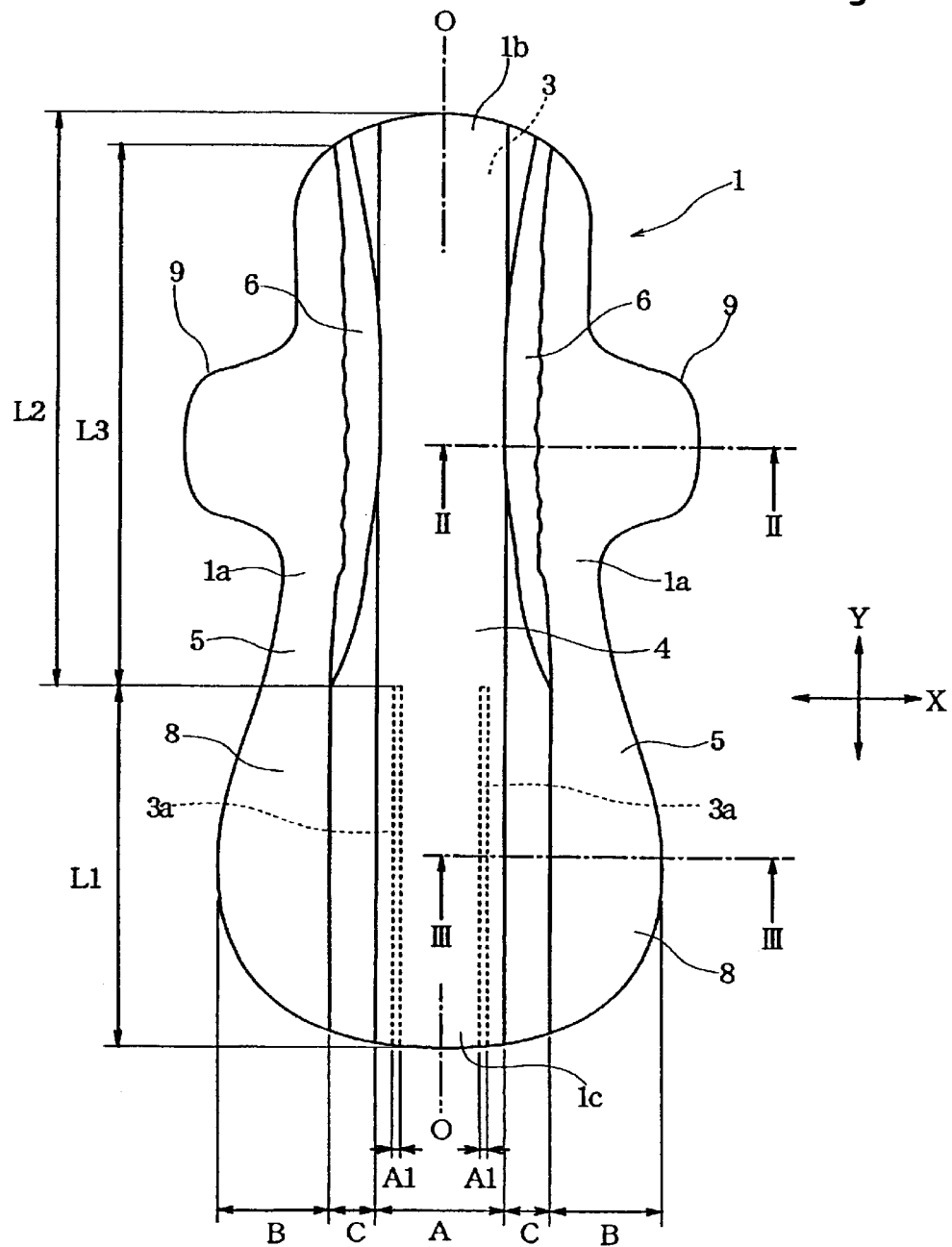
FIG. 1 is a top plan view showing a sanitary napkin according to one embodiment of the invention.
Figure 2:
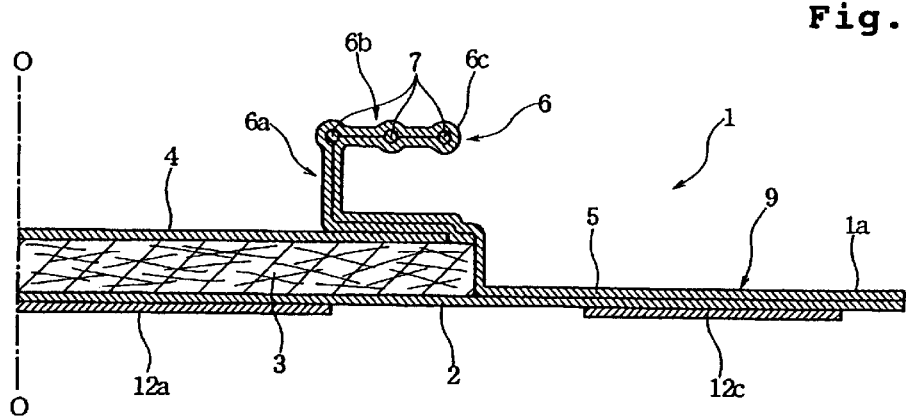
FIG. 2 is a sectional view of one half taken along line II—II of FIG. 1.
Figure 3:
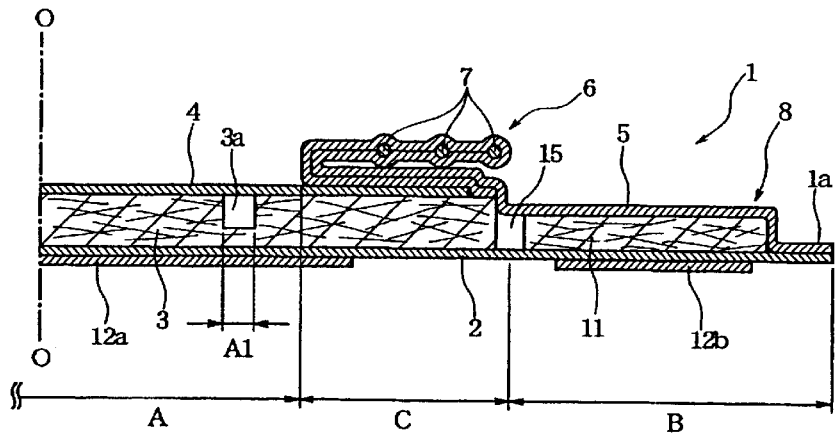
FIG. 3 is a sectional view of one half taken along line III—III of FIG. 1.
Figure 4:
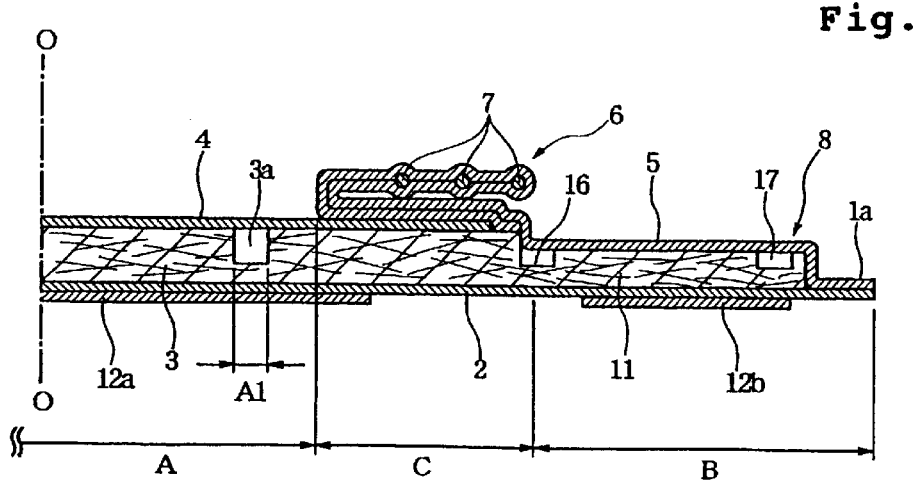
FIG. 4 is a sectional view of one half corresponding to FIG. 3 but shows a sanitary napkin according to another embodiment of the invention.
Figure 5:
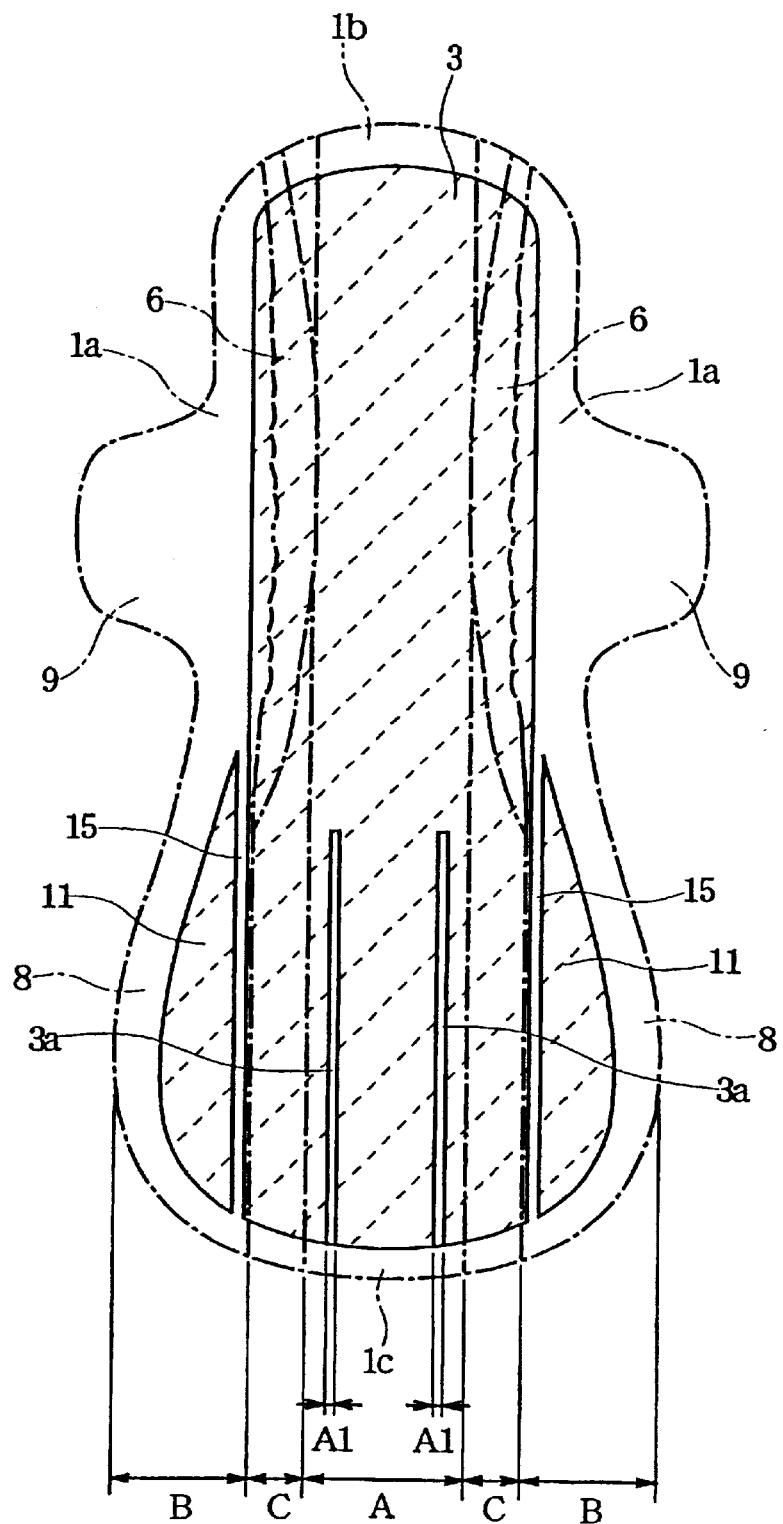
FIG. 5 is a perspective top plan view showing the shapes of a main absorbent core and auxiliary absorbent cores of the sanitary napkin shown in FIG. 1.
Figure 6:
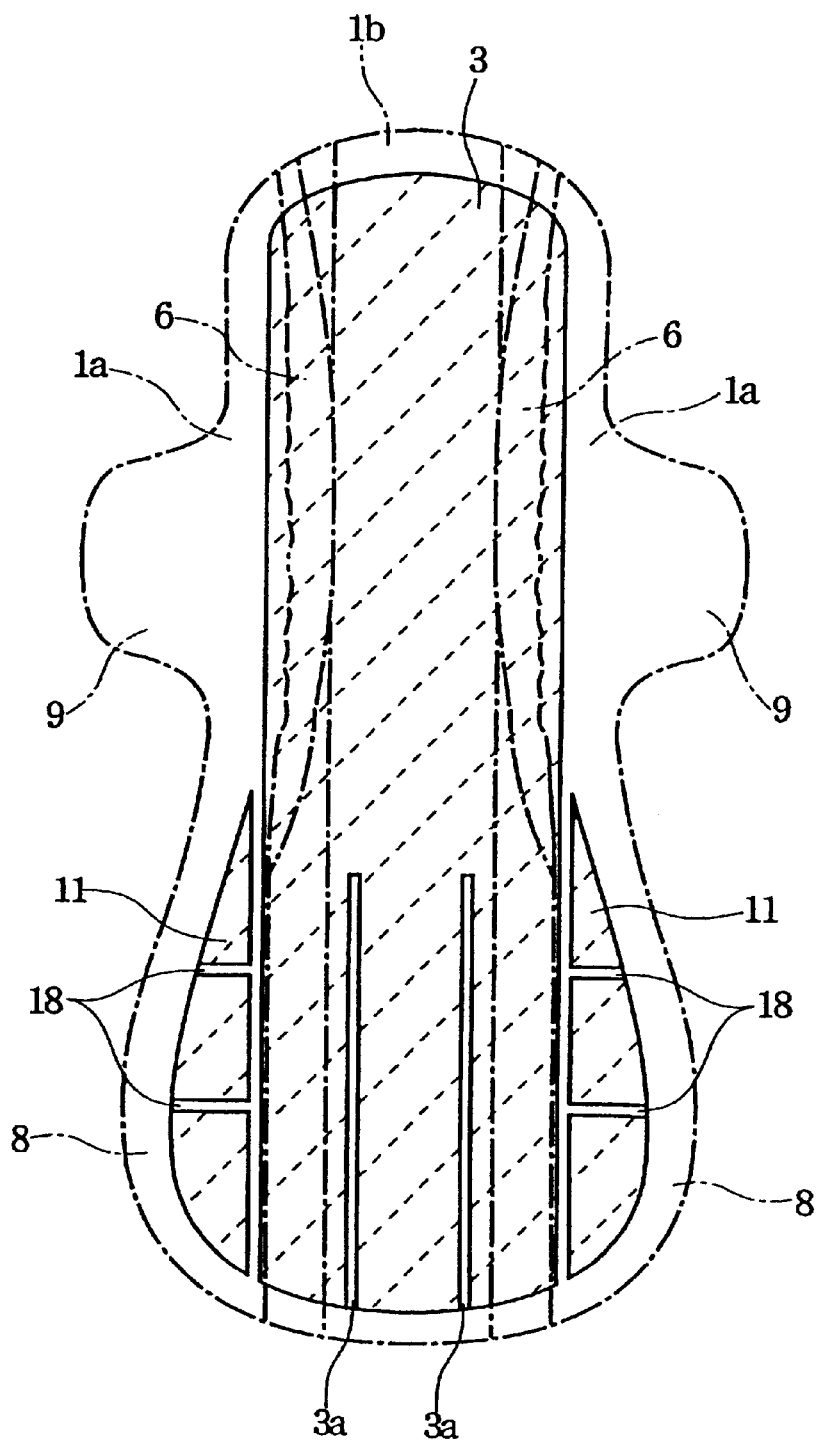
FIG. 6 is a perspective top plan view corresponding to FIG. 5 but shows a sanitary napkin according to still another embodiment of the invention.

FIG. 1 is a top plan view showing a sanitary napkin according to one embodiment of the invention; FIG. 2 is a sectional view of one half taken along line II—II of FIG. 1; FIG. 3 is a sectional view of one half taken along line III—III of FIG. 1; FIG. 4 is a sectional view of one half corresponding to FIG. 3 but shows a sanitary napkin according to another embodiment of the invention; FIG. 5 is a perspective top plan view showing the shapes of a main absorbent core and auxiliary absorbent cores of the sanitary napkin shown in FIG. 1; and FIG. 6 is a perspective top plan view corresponding to FIG. 5 but shows a sanitary napkin according to still another embodiment of the invention. Here, FIGS. 2, 3 and 4 are sectional views each showing one side half of a centerline O—O extending in a longitudinal direction of a sanitary napkin, with the other side half being given a symmetrical structure.

A sanitary napkin 1, as shown in FIGS. 1 to 3, is made symmetric with respect to the centerline O—O extending in the longitudinal direction (or Y-direction) thereof. In the sanitary napkin 1: a central portion extending in the longitudinal direction with a predetermined width is a main absorbent region A; portions on both left and right sides thereof are side regions B and B; and portions between the main absorbent region A and the side regions B and B are boundary regions C and C. Of the main absorbent region A, moreover, there are formed stiff portions A1 and A1 where the stiffness is enhanced.

In the sanitary napkin 1, on the other hand, a portion extending from the rear end of the napkin 1 to a predetermined length is a rear portion L1, in which rear flaps (as will be described hereinafter) and the stiff portions A1 are formed; and the remaining portion forwardly of the rear portion L1 is a front portion L2. In the embodiment shown, a leakage-preventing region L3, in which leakage-preventing side walls (as will be described hereinafter) are allowed to rise over a predetermined length, is positioned within the front portion L2. However, the leakage-preventing region L3 may be extended either to midway of or over the substantially entire length of the rear portion L1.

As shown in FIGS. 2 and 3, the sanitary napkin 1 is provided all over its back with a back sheet 2 made of a liquid-impermeable sheet. Over the back sheet 2, there is laid a main absorbent core 3. As shown in FIG. 5, the main absorbent core 3 is formed to have a width size substantially equal to the sum of the widths of the main absorbent region A and the boundary regions C and C and to extend over almost the entire length of the napkin 1.

On the surface side (or a liquid receiving side) of the sanitary napkin 1, there is disposed a liquid-permeable surface sheet 4 which covers the main absorbent core 3. This surface sheet 4 is formed to have a width size substantially equal to the sum of the widths of the main absorbent region A and the boundary regions C and C and to extend over the entire length of the napkin 1.

On the liquid receiving side of the sanitary napkin 1, moreover, there are disposed liquid-impermeable or hydrophobic side sheets 5 and 5, which cover regions outside of the main absorbent region A. As shown in FIGS. 2 and 3, each side sheet 5 is folded in the boundary region C to have a larger thickness than in the side region B. The folded portion of each side sheet 5 is referred to as "leakage-preventing side wall 6". Between confronting faces of the folded portion of each side sheet 5, there are sandwiched and adhered a plurality of (e.g., three, as shown in the drawings) elastic members 7, which extend over the substantially entire length of the leakage-preventing side wall 6.

In the rear portion L1, as shown in FIG. 3, each leakage-preventing side wall 6 is adhered or fused on the surface of the surface sheet 4, while being folded into a generally flat state. Similarly, each leakage-preventing side wall 6 is also folded into a generally flat state and adhered or fused on the surface of the surface sheet 4 in a portion of the front portion L2 forwardly of the leakage-preventing region L3. In the leakage-preventing region L3, on the other hand, a portion of each leakage-preventing side wall 6 is set free.

When the sanitary napkin 1 is in a free state with no external force applied, it is concavely curved on its liquid receiving side by the elastic shrinking force of the elastic members 7. As a result, the free portion of each leakage-preventing side wall 6 is raised in the leakage-preventing region L3, as shown in FIG. 2, to have a wall portion 6a rising upwardly from the surface sheet 4 and a skin-contacting portion 6b extending from the upper portion of the wall portion 6a with its free end 6c directed outwardly of the napkin 1.

As shown in FIGS. 1, 2, 3 and 5, the back sheet 2 is joined to the side sheets 5 at left and right peripheral portions 1a and 1a where no absorbent core is present. On the other hand, the back sheet 2 is joined to the surface sheet 4 at front and rear peripheral portions 1b and 1c where no absorbent core is present, as shown in FIGS. 1 and 5. The joining is effected either by an adhering method using a hot-melt type adhesive or by a thermal fusing method (or a heat sealing method).

In the rear portion L1 of the sanitary napkin 1, as shown in FIGS. 1 and 5, the side regions B and B are protruded in a width direction (or X-direction) of the napkin 1 to form rear flaps 8 and 8 having curved edges. In the front portion L2, on the other hand, the side regions B and B are protruded in the width direction to form wings 9 and 9. This sanitary napkin 1 is used such that the wings 9 and 9 are folded back to clamp the crotch portion of an underwear. On the other hand, the rear flaps 8 and 8 are applied to the buttocks of a wearer.

At the rear flaps 8 and 8, as shown in FIGS. 3 and 5, auxiliary absorbent cores 11 are each disposed between the back sheet 2 and the side sheet 5. At the wings 9 and 9, on the other hand, the back sheet 2 and the side sheet 5 are joined to each other, as shown in FIGS. 2 and 5.

The sanitary napkin 1 is provided on the outer face of the back sheet 2 with adhesive layers, through which it is adhered to an underwear. On the outer face of the back sheet 2, as shown in FIGS. 2 and 3: an adhesive layer 12a is disposed on the substantial back side of the main absorbent region A; adhesive layers 12b and 12b are disposed on the rear flaps 8 and 8; and adhesive layers 12c and 12c are disposed on the wings 9 and 9.

When the sanitary napkin 1 is to be worn, the adhesive layer 12a is adhered to the inner face of the crotch portion of an underwear, and the adhesive layers 12b and 12b are adhered to the back portion of the underwear. Then, the wings 9 and 9 are folded back to wrap the two sides of the crotch portion of the underwear therein so that the adhesive layers 12c and 12c are adhered to the outer face of the crotch portion of the underwear.

The main absorbent core 3 is formed from a hydrophilic material, such as air-laid pulp, a laminate of thin paper or polymer sheet, accumulated (deposited) fluff pulp or natural cellulose fibers, a combination of these, or a mixture of these, and is given a width of about 50 to 100 mm. For example, the main absorbent core 3 is prepared by accumulating fluff pulp to have a basis weight in a range of 200 to 500 $g/m^2$, by coating it with thin paper, and by pressing the coated accumulation to have a density of 50 to 120 $mg/cm^3$. Here, it is also possible to admix 5 to 40 wt. % of superabsorbent polymer (SAP) in the accumulated fluff pulp to block the migration of the liquid inside of the main absorbent core 3 with absorbency of the superabsorbent polymer.

As shown in FIGS. 1 and 5, the main absorbent core 3 is provided, at the rear portion L1, i.e., at the region having the rear flaps 8 and 8, with compressed portions (or pressed portions) 3a and 3a, which extend linearly in the longitudinal direction so that they and their surrounding portions provide the stiff portions A1 and A1. These linear compressed portions 3a and 3a are formed in symmetrical relation about the centerline O—O and are arranged in parallel with each other. Of course, a plurality of linear compressed portions may be formed in each of the left and right sides of the main absorbent core 3 in such a parallel and symmetrical relation.

The compressed portions 3a are formed in the main absorbent region A. Here, each compressed portion 3a has a width in a range of 2 to 5 mm, and the main absorbent region A has a width in a range of 20 to 60 mm.

The auxiliary absorbent cores 11 may be made of the same material as that of the main absorbent core 3. In this case, the basis weight of the auxiliary absorbent core 11 may be equal to but preferably smaller than that of the main absorbent core 3. For example, the main absorbent core 3 and the auxiliary absorbent cores 11 are formed from hydrophilic fiber accumulations, which are separated from one another on boundary lines between the boundary regions C and the side regions B, and enveloped with common tissue paper. As a result, on the boundary lines between the boundary regions C and the side regions B, there are formed folding portions (fold-facilitating portions) 15 and 15, in which no absorbent core is present except for the tissue paper. That is, the main absorbent core 3 and the auxiliary absorbent cores 11 are substantially separated from one another by the folding portions 15 and 15.

Alternatively, the auxiliary absorbent cores 11 may be made of a material different from that of the main absorbent core 3. In this case, for example, the auxiliary absorbent core 11 may be formed from a through-air bonded nonwoven fabric having a high cushioning property, a hydrophilic foamed resin sheet, or a foamed sheet treated to be hydrophilic, and may be completely separated from the main absorbent core 3.

The liquid-permeable surface sheet 4 may be formed from a nonwoven fabric, such as a nonwoven fabric of hydrophobic fibers and hydrophilic fibers or an apertured nonwoven fabric (i.e., nonwoven fabric with a plurality of through holes) of hydrophobic fibers, or a porous film. The surface sheet 4 may be formed so bulky as to provide improved fitness (improved conformity to the wearer's body) and may preferably have a bulk thickness in a range of about 1 to 15 mm.

The back sheet 2 may be formed from an air-permeable (breathable) resin film, a nonwoven fabric of hydrophobic fibers, or a laminate of the nonwoven fabric and the film.

The side sheet 5 forming the leakage-preventing side wall 6 may be made of a nonwoven fabric of hydrophobic synthetic fibers, a foamed sheet, a porous film or an apertured nonwoven fabric (i.e., nonwoven fabric with a plurality of through holes). Examples of other suitable materials include: a nonwoven fabric prepared by treating hydrophobic synthetic fibers to be hydrophilic and by making them into a sheet; and a sheet prepared by blending hydrophobic synthetic fibers with hydrophilic fibers such as viscose rayon, acetate rayon or natural cellulose fibers. Here, it is possible to provide an absorbent material (such as a SAP sheet prepared by wrapping superabsorbent polymer with tissue paper, air-laid pulp, a hydrophilic melt-blown nonwoven fabric, a pulp sheet, or a spun-laced nonwoven fabric of rayon) inside of the leakage-preventing side walls 6 and 6 made of the aforementioned material, so that the liquid, as coming into contact with the leakage-preventing side walls 6 and 6, can be absorbed and retained therein.

The elastic members 7 may be made of a film-, filament- or net-shaped material composed mainly of thermoplastic synthetic rubber, or a sheet- or filament-shaped material composed mainly of natural rubber, and are preferably adhered to and fixed on the leakage-preventing side walls 6 and 6 while being extended within a range of 1.1 to 2.0 times its original length and applied with a force within a range of 0.49 to 1.47 N.

Here, when the free portions of the leakage-preventing side walls 6 and 6 are raised, as shown in FIG. 2, the wall portions 6a have a height of 5 to 50 mm and the skin-contacting portions 6b have a width of 5 to 30 mm.

In the rear portion L1 having the rear flaps 8 and 8, the side sheet 5 are individually folded and laminated at the boundary regions C to form the leakage-preventing side walls 6 in such a generally flat state as shown in FIG. 3 (although the leakage-preventing side walls 6 may also rise in at least a portion of the rear portion L1). Therefore, the sanitary napkin 1 is made bulky in the boundary regions C, as shown in the sectional view of FIG. 3.

In the rear portion L1, a portion having the stiff portion A1 (i.e., a portion having the compressed portion 3a) within the main absorbent region A, the side region B having the rear flap 8, and the boundary region C having the leakage-preventing side wall 6 have different stiffnesses according to the following relationship: the portion having the stiff portion A1>the boundary region C>the rear flap.

Here, the stiffnesses were measured in accordance with JIS L-1096, A method (Gurley method), by using Gurley's stiffness tester (Type 311; manufactured by Yasuda Seiki), for the samples which were cut to extend in the longitudinal direction (or Y-direction) of the sanitary napkin 1 with a width of 10 mm in the width direction (or X-direction). In the main absorbent region A, the sample is given the width of 10 mm having the compressed portion 3a therein (if a plurality of compressed portions are formed in each of the left and right sides, the sample may have a plurality of compressed portions within the width of 10 mm). In the boundary region C, the sample is given the width of 10 mm having the leakage preventing side wall 6 therein.

It is preferred that the portion of the main absorbent region A having the stiff portions A1 therein is given a stiffness of 9.8 to 29.4 mN, that the boundary region C is given a stiffness of 3.94 to 8.8 mN, and that the side region B having the rear flap is given a stiffness of 0.49 to 3.43 mN.

The sanitary napkin 1 is provided at the rear portion L1 with the rear flaps 8 and 8, which are shaped to bulge in the width direction thereof and applied to the buttocks of a wearer in use. Therefore, these rear flaps 8 and 8 can prevent the menstrual blood from leaking sideways from the buttocks while the wearer is sleeping.

In the rear portion L1, the main absorbent region A is provided with the stiff portions A1 so that the main absorbent region A can be hardly folded or twisted and can be prevented from leaving or going out of position from the skin of a wearer.

On both the sides of the main absorbent region A, there are located the boundary regions C which are bulky with the leakage-preventing side walls 6 and stiffer than the rear flaps 8. These boundary regions C are so bulky as to have a high cushioning property and provide a soft contact with the wearer's skin. Because of the proper stiffness, moreover, the boundary regions C are hardly twisted, slid or folded to overlap the main absorbent region A.

In the rear flaps 8 and 8, on the other hand, there are disposed the auxiliary absorbent cores 11 which can absorb the menstrual blood having flown to the rear flaps 8 thereby to prevent the sideway leakage from the sanitary napkin 1 effectively. Because of the low stiffness, moreover, the rear flaps 8 easily fit on the buttocks while following their shapes. With the folding portions 15, the rear flaps 8 easily fit on the buttocks while following their curves.

Between the rear flaps 8 of the relatively low stiffness and the main absorbent region A, there are present the boundary regions C which are stiffer than the rear flaps 8, so that these rear flaps 8 hardly overlap the main absorbent region A even if they are twisted or deformed. Therefore, the overlap between the rear flaps 8 and the main absorbent region A is hardly caused by the fold or twist so that the absorbent capacity of the main absorbent region A is hardly lowered and uncomfortable feeling to the wearer's skin is hardly caused.

In an embodiment shown in FIG. 4, the main absorbent core 3 and the auxiliary absorbent cores 11 merge into one another at the rear portion L1. On the boundary lines between the boundary regions C and the rear flaps 8, however, the integrated absorbent core is compressed or reduced in thickness to form folding portions 16 as the boundary lines between the main absorbent core 3 and the auxiliary absorbent cores 11. Moreover, compressed portions 17 are so formed in the edge portions of the auxiliary absorbent cores 11 as to extend along the outer peripheral edges of the rear flaps 8.

When the menstrual blood arrives at the rear flaps 8 to be absorbed by the auxiliary absorbent cores 11 and migrates sideways in or on the auxiliary absorbent cores 11, this menstrual blood is drawn and held by the compressed portions 17 having a high density. Therefore, the menstrual blood is hardly allowed to leak farther from the rear flaps 8.

Next in an embodiment shown in FIG. 6, the auxiliary absorbent cores 11, as disposed in the rear flaps 8 and 8, are substantially or completely separated on separate lines to form folding portions 18. Alternatively, the folding portions 18 may be formed by compressing the auxiliary absorbent cores 11. By these folding portions 18, the individual auxiliary absorbent cores 11 are split into a plurality of segments in the longitudinal direction. In this embodiment, the auxiliary absorbent core 11 is easily curved in the longitudinal direction so that it can be more deformed to follow the shape of the buttocks of a wearer.

Here in the rear portion L1, the main absorbent region A may be formed substantially in its entirety into the stiff portion A1, for example, by compressing the main absorbent core 3 entirely in the main absorbent region A on the side of the rear portion L1 so as to have a stiffness higher than that in the front portion L2.

According to the invention, as has been described in detail, the sanitary napkin can be prevented from having its rear flaps wrapped in while being worn especially in sleep. Therefore, neither the absorbing function nor the fitness of the main absorbent region is deteriorated. On the other hand, the rear flaps have the liquid absorbing function so that they can prevent the sideway liquid leakage effectively.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary napkin having a longitudinal rear portion to be applied to the buttocks of a wearer, comprising:

a longitudinally extending main absorbent region in which a longitudinally extending main absorbent core is disposed between a liquid-impermeable back sheet and a liquid-permeable surface sheet;

side regions positioned on both sides of said main absorbent region; and boundary regions between said main absorbent region and said side regions, each boundary region being provided with a longitudinally extending leakage-preventing side wall, wherein in said rear portion, at least a portion of said main absorbent region is formed into a stiff portion having a stiffness higher than that of the remaining portion of said main absorbent region, and in said rear portion, said side regions are protruded laterally to form rear flaps, in each of which an auxiliary absorbent core is disposed between said back sheet and a sheet positioned on a surface side opposite to said back sheet with respect to said auxiliary absorbent core, wherein in said rear portion, a portion of said main absorbent region having said stiff portion therein, said boundary region and said rear flap have different longitudinal stiffnesses according to the following relationship: said portion of said main absorbent region having said stiff portion therein>said boundary region>said rear flap.

2. The sanitary napkin as set forth in claim 1, wherein said portion of said main absorbent region having said stiff portion therein has a stiffness of 9.8 to 29.4 mN; said boundary region has a stiffness of 3.94 to 8.8 mN; and said rear flap has a stiffness of 0.49 to 3.43 mN.

3. The sanitary napkin as set forth in claim 1, wherein in said rear portion, said main absorbent core is compressed at least partially to form said stiff portion.

4. The sanitary napkin as set forth in claim 3, wherein in said rear portion, said main absorbent core is partially compressed so that said stiff portion extends linearly in the longitudinal direction.

5. The sanitary napkin as set forth in claim 1, wherein each leakage-preventing side wall is folded and secured in said rear portion so as not to allow of rising thereof, but is allowed to rise from said surface side in a portion forwardly of said rear portion.

6. The sanitary napkin as set forth in claim 1, wherein folding portions for facilitating folding of said rear flaps are formed on boundary lines between said boundary regions and said rear flaps.

7. The sanitary napkin as set forth in claim 6, wherein said main absorbent core and said auxiliary absorbent cores are separated from one another at said folding portions.

8. The sanitary napkin as set forth in claim 1, wherein each auxiliary absorbent core is split into a plurality of segments.

\* \* \* \* \*